United States Patent
Ham et al.

(10) Patent No.: US 9,658,138 B2
(45) Date of Patent: May 23, 2017

(54) CONTAINER FIXING HOLDER OF TIME-SERIES SEDIMENT TRAPPING DEVICE

(71) Applicant: KOREA INSTITUTE OF OCEAN SCIENCE & TECHNOLOGY, Ansan-si, Gyeonggi-do (KR)

(72) Inventors: Dong-Jin Ham, Ansan-si (KR); Gun-Chang Lee, Gunpo-si (KR); Sang-Bum Chi, Seoul (KR); Kyeong-Hong Kim, Gunpo-si (KR); Hyoung-Jeek Kim, Gunpo-si (KR)

(73) Assignee: Korea Institute of Ocean Science & Technology, Ansan-si (KR)

( * ) Notice: Subject to any disclaimer, the term of this patent is extended or adjusted under 35 U.S.C. 154(b) by 0 days.

(21) Appl. No.: 14/900,089

(22) PCT Filed: Jun. 9, 2014

(86) PCT No.: PCT/KR2014/005047
§ 371 (c)(1),
(2) Date: Dec. 18, 2015

(87) PCT Pub. No.: WO2014/204121
PCT Pub. Date: Dec. 24, 2014

(65) Prior Publication Data
US 2016/0146713 A1 May 26, 2016

(30) Foreign Application Priority Data

Jun. 20, 2013 (KR) ........................ 10-2013-0071188

(51) Int. Cl.
*G01N 1/00* (2006.01)
*G01N 1/20* (2006.01)
(Continued)

(52) U.S. Cl.
CPC ............. *G01N 1/2035* (2013.01); *E02B 1/00* (2013.01); *G01N 1/18* (2013.01); *E02D 1/04* (2013.01);
(Continued)

(58) Field of Classification Search
None
See application file for complete search history.

(56) References Cited

U.S. PATENT DOCUMENTS 4,321,823 A * 3/1982 Anderson .......... G01N 33/1886
222/57
5,085,085 A * 2/1992 Anderson ................ G01N 1/02
73/863.02

FOREIGN PATENT DOCUMENTS

JP 2009-294139 12/2009
JP 2011-185737 9/2011
KR 10-2012-0029809 3/2012

OTHER PUBLICATIONS

International Search Report of corresponding PCT/KR2014/005047, dated Jul. 31, 2014, 4 pages.
(Continued)

*Primary Examiner* — Robert R Raevis
(74) *Attorney, Agent, or Firm* — Lewis Roca Rothgerber Christie LLP

(57) ABSTRACT

Disclosed is a container fixing holder of a time-series sediment trapping device. With respect to the container fixing holder of the time-series sediment trapping device, the time-series sediment trapping device includes a funnel; a frame disposed to support and surround the funnel, a frame having at least one rod vertically disposed and a fixing plate coupled to the at least one rod forming the frame on a horizontal plane defined by a lower portion of the funnel, wherein a rotation plate, to which a plurality of time-series sediment trapping containers to trap the time-series sediment
(Continued)

collected through the funnel are fixedly attached, is formed under the fixing plate. The container fixing holder includes a circular holder for fixing the plurality of time-series sediment trapping containers fixedly attached to the rotation plate without shaking.

12 Claims, 4 Drawing Sheets

(51) Int. Cl.
*G01N 1/18* (2006.01)
*E02B 1/00* (2006.01)
*G01N 1/10* (2006.01)
*E02D 1/04* (2006.01)
*G01N 1/40* (2006.01)

(52) U.S. Cl.
CPC ............... *G01N 2001/1025* (2013.01); *G01N 2001/1031* (2013.01); *G01N 2001/2071* (2013.01); *G01N 2001/4083* (2013.01)

(56) References Cited

OTHER PUBLICATIONS

Susumu Hongjo, "Catching the Rain. Sediment Trap Technology," Oceanus Oct. 1997, vol. 40, No. 2, p. 8 and 9.

\* cited by examiner

CONTAINER FIXING HOLDER OF TIME-SERIES SEDIMENT TRAPPING DEVICE

CROSS-REFERENCED TO RELATED APPLICATIONS

This Application is a National Phase Patent Application and claims priority to and the benefit of International Application Number PCT/KR2014/005047, filed on Jun. 9, 2014, which claims priority to and the benefit of Korean Application 10-2013-0071188, filed Jun. 20, 2013, the entire contents of all of which are incorporated herein by reference.

TECHNICAL FIELD

The present invention relates to a container fixing holder of a time-series sediment trapping device, and more particularly to a container fixing holder of a time-series sediment trapping device, capable of preventing a container from being broken or missed during the time-series trapping of sediment into the container installed in the trapping device installed on the seabed to trap the sediment transferred from the sea in time series.

BACKGROUND ART

As organic matters or minerals dropped down from the surface of the sea are continuously accumulated, sediment is formed under water or on the seabed.

When the sediment is trapped and analyzed, the total amount of sediment deposited on a relevant water zone can be easily detected.

To this end, there has been invented a device which is fixedly installed at a specific place and supported for a predetermined time to trap the sediment in time series.

In detail, for trapping the sediment, there is suggested a time-series sediment trapping device having a plurality of time-series sediment trapping containers fixedly attached thereto and including a funnel to collect the sediment dropped down under water. The time-series sediment trapping device is generally positioned on the bottom of a lake or the sea to trap the sediment for a long time.

Hereinafter, the time-series sediment trapping device according to the related art will be described in brief.

FIG. 1 is a schematic sectional view showing the time-series sediment trapping device according to the related art, and FIG. 2 is a schematic sectional view showing a main part of the time-series sediment trapping device according to the related art.

Referring to FIG. 1, the time-series sediment trapping device according to the related art includes a funnel 10 to collect sediment dropped down under water, a frame 20 disposed to support and surround the funnel and having at least one rod vertically disposed, and a fixing plate 24 coupled to the at least one rod forming the frame 20 on a horizontal plane defined by a lower portion of the funnel. A rotation plate 30, to which a plurality of time-series sediment trapping containers 36 to trap the time-series sediment collected through the funnel 10 are fixedly attached, is formed on a lower portion of the fixing plate 24. The rotation plate 30 time-series-rotates via gear-engagement through the rotation of a motor 50 to trap the time-series sediment into the time-series sediment trapping container 36.

It is preferred that the fixing plate 24 and the rotation plate 30 are vertically arranged, and a portion of the rotation plate 30 is inserted into the fixing plate 24, and the details of the detailed structures of the fixing plate 24 and the rotation plate 30 will be omitted. The coupling relationship between the fixing plate 24 and the rotation plate 30 is well known to those skilled in the art even though the details of the detailed structures of the fixing plate 24 and the rotation plate 30 are omitted.

The sediment is trapped from a top surface 12 of the funnel 10 into one of a plurality of time-series sediment trapping containers 36 through a neck 16 of the funnel 10 and a trapping hole 31 commonly formed through the fixing plate 24 and the rotation plate 30 provided under the fixing plate 24.

In this case, the sediment may be exactly trapped into one of the time-series sediment trapping containers 36 by guides 14 formed to surround the neck 16 of the funnel.

Reference number 40 of FIG. 1 preferably represents a control unit 40 including a controller to control the overall operations of the time-series sediment trapping device and a battery to ensure the operation of the time-series sediment trapping device under water for a long time.

Preferably, the configurations of an upper end support 20 and a lower end support 26 are further provided at upper and lower ends of the frame 20 constituting the time-series sediment trapping device.

In addition, a mooring hole 21 is preferably further formed in the upper most end of the rod constituting the frame 20 to moor the time-series sediment trapping device. Alternatively, the mooring hole 21 may be formed in the shape of a ring.

In addition, a weight hole 28 may be formed in a lower end of the frame 20 of the time-series sediment trapping device and used to stably drop down the time-series sediment trapping device. When the time-series sediment trapping device is positioned on the bottom of a lake or the sea, a weight may be attached into the weight hole 28.

Hereinafter, a main part of the time-series sediment trapping device according to the related art will be described with reference to FIG. 2.

Since most elements represented in reference numerals 10, 14, 16, and 24 of FIG. 2 are the same as those of FIG. 1, the details thereof will be omitted.

As shown in FIG. 2, the rotation plate 30 is formed at an outer circumference thereof with a gear 33, and the gear 33 is engaged with a gear part 34 of a motor 50. Accordingly, when the motor 50 is rotated, the rotation plate 30 is rotated due to the engagement rotation of the gear part 34. Accordingly, one (shown in reference numeral 2 of FIG. 2) of the time-series sediment trapping containers 36 fixedly coupled to the rotation plate 30 may trap the sediment.

In this case, the time-series sediment trapping containers 36 are preferably screwed with the rotation plate 30. The screw-coupling of one 2 of the time-series sediment trapping containers 36 may be recognized through a threaded part 32 as shown in FIG. 2.

Although numbers are marked in the time-series sediment trapping containers 36 as shown in FIG. 2, the numbers are used only for illustrating the sequence of trapping the sediment when trapping the sediment in time series, and the identified numbers or the inherent sequence of the time-series sediment trapping containers 36 may be expressed in various manners.

When the motor 50 is rotated, the sediment may be first trapped into the time-series sediment trapping container 36 marked in "1" among the time-series sediment trapping containers 36.

For example, as the motor 50 is rotated after a predetermined time, for example, one month or 15 days have been elapsed, the time-series sediment trapping container 36 expressed in "1" is moved to a different position of the fixing plate 24, so that the additional trapping of the sediment may be stopped.

In this case, preferably, the structure of preventing external sediment from being disorderly introduced is further provided.

As described above, after trapping predetermined sediment into the time-series sediment trapping container 36, the time-series sediment trapping container 36 having predetermined sediment, which is trapped, is recovered by lifting a wire (not shown) fixed to the mooring hole 21.

In this case, a portion of the time-series sediment trapping container 36 may be broken, lost, or missed, which is considered to be caused by a strong tidal current. When a portion of the time-series sediment trapping container 36 is broken, lost, or missed, data of the portion of the time-series sediment are omitted. Accordingly, it is necessary to prevent the time-series sediment trapping container from being broken or missed to acquire perfect data in time series when trapping the time-series sediment.

As a prior art related to the present invention, there is U.S. Pat. No. 7,069,771 (published on Jul. 4, 2006) (Title of the Invention: "Partitioning sediment trap").

DISCLOSURE

Technical Problem

An object of the present invention is to fix a time-series sediment trapping container of a time-series sediment trapping device by a container fixing holder to prevent the time-series sediment trapping container from being broken or missed, so that perfect data can be acquired in time series when the time-series sediment is trapped.

The objects of the present invention are not limited to the above-mentioned objects, and other objects will be clearly understood from the following description by those skilled in the art.

Technical Solution

In order to accomplish the above object, there is provided a container fixing holder of a time-series sediment trapping device. The time-series sediment trapping device includes a funnel to collect sediment dropped under water, a frame provided to support and surround the funnel and having at least one rod vertically provided, and a fixing plate coupled to the at least one rod forming the frame on a horizontal plane defined by a lower portion of the funnel, a rotation plate, to which a plurality of time-series sediment trapping containers to trap time-series sediment collected through the funnel are fixedly attached, is formed under the fixing plate, the rotation plates rotates in time series via gear-engagement through rotation of a motor such that the time-series sediment is trapped into the time-series sediment trapping container, and a circular holder is included to fix the time-series sediment trapping containers fixedly attached to the rotation plate without shaking.

According to an exemplary embodiment of the present invention, preferably, the time-series sediment trapping containers are fixed to the rotation plate.

According to an exemplary embodiment of the present invention, preferably, at least one support, which extends downward, is fixed to the rotation plate.

According to an exemplary embodiment of the present invention, preferably, the support extending downward from the rotation plate is fixed to the circular holder while extending until the circular holder.

According to an exemplary embodiment of the present invention, preferably, the support is fixed to the rotation plate in screw-type coupling.

According to an exemplary embodiment of the present invention, preferably, the support is further fixed to the rotation plate by a bolt.

According to an exemplary embodiment of the present invention, preferably, the support is fixed to upper and lower portions of the circular holder by a bolt and a nut.

According to an exemplary embodiment of the present invention, preferably, the circular holder is formed therein with a plurality of mounting holes into which the time-series sediment trapping containers are securely mounted.

According to an exemplary embodiment of the present invention, preferably, the mounting holes formed in the circular holder are formed corresponding to positions of the time-series sediment trapping containers.

According to an exemplary embodiment of the present invention, preferably, the fixing plate and the rotation plate include plastic.

According to an exemplary embodiment of the present invention, preferably, the frame is formed in an upper end thereof with a mooring hole to moor the time-series sediment trapping device.

According to an exemplary embodiment of the present invention, preferably, the frame is provided therein with a weight hole to stably drop the time-series sediment trapping device.

Details of other embodiments are included in the detailed description and the accompanying drawings. The advantages, the features, and schemes of achieving the advantages and features of the present invention will be apparently comprehended by those skilled in the art based on the embodiments, which are detailed later in detail, together with accompanying drawings. The present invention is not limited to the following embodiments but includes various applications and modifications. The embodiments will make the disclosure of the present invention complete, and allow those skilled in the art to completely comprehend the scope of the present invention. The present invention is only defined within the scope of accompanying claims.

The same reference numerals are assigned to the same elements throughout the specification, and sizes, positions, and coupling relationships of the elements constituting the invention may be exaggerated for clarity.

Advantageous Effects

As described above, according to the present invention, since the time-series sediment trapping container of the time-series sediment trapping device is fixed by the container fixing holder, the time-series sediment trapping container are not broken or missed, so that perfect data can be acquired in time series when the time-series sediment is trapped.

BEST MODE

Mode for Invention

The advantages, the features, and schemes of achieving the advantages and features will be apparently comprehended by those skilled in the art based on the embodiments, which are detailed later in detail, together with accompanying drawings. The present invention is not limited to the following embodiments but includes various applications and modifications. The embodiments will make the disclosure of the present invention complete, and allow those skilled in the art to completely comprehend the scope of the present invention.

Hereinafter, a container fixing holder of a time-series sediment trapping device according to an exemplary embodiment of the present invention will be described with reference to accompanying drawings.

Figure 3:
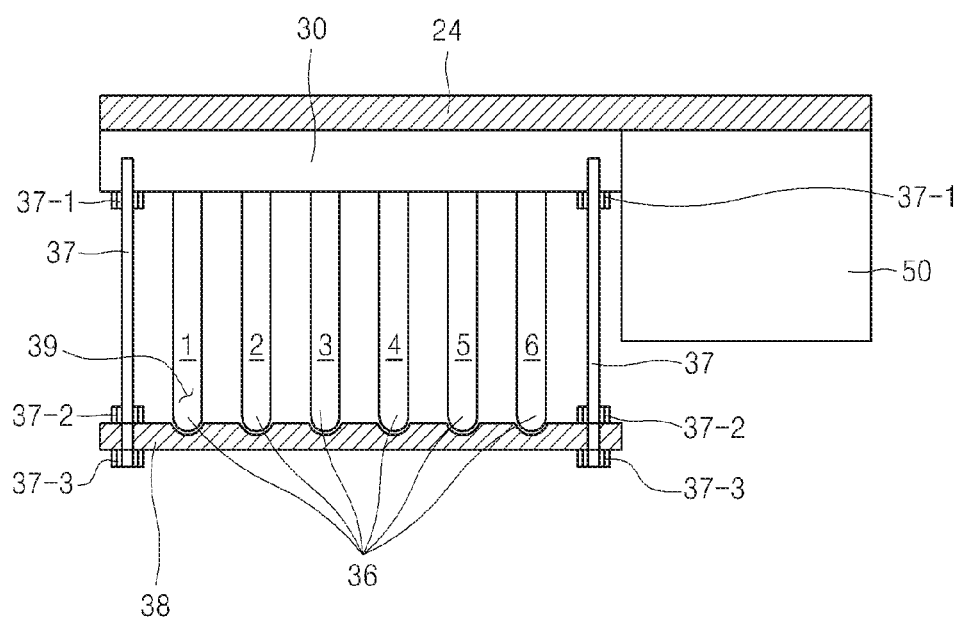
FIG. 3 is a schematic sectional view showing a container fixing holder of a time-series sediment trapping device according to an exemplary embodiment of the present invention.

FIG. 3 is a schematic sectional view showing a container fixing holder of a time-series sediment trapping device according to an exemplary embodiment of the present invention.

Figure 1:
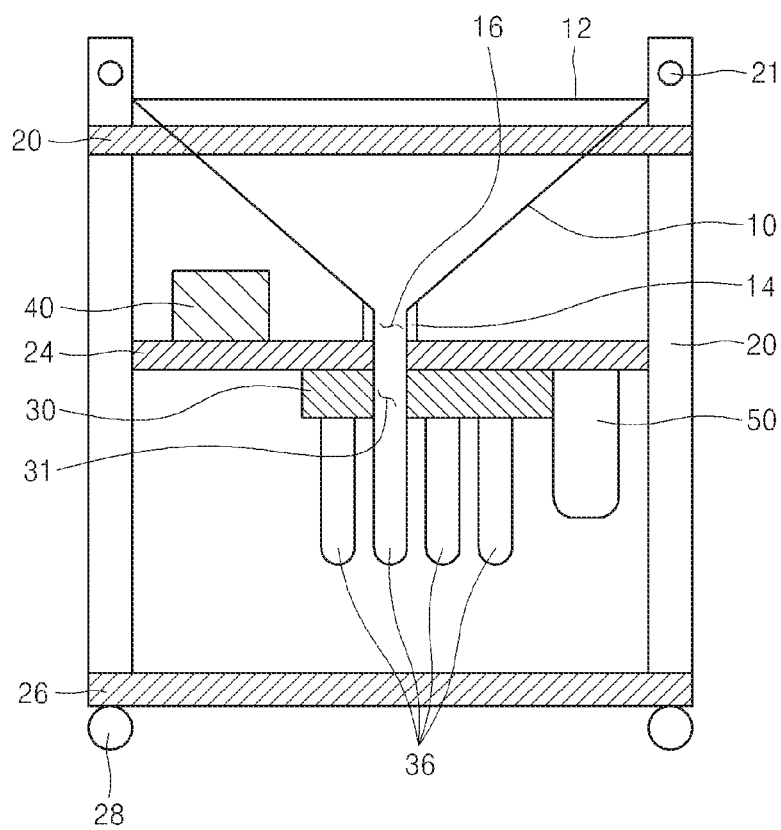
FIG. 1 is a schematic sectional view showing a time-series sediment trapping device according to the related art.
Figure 2:
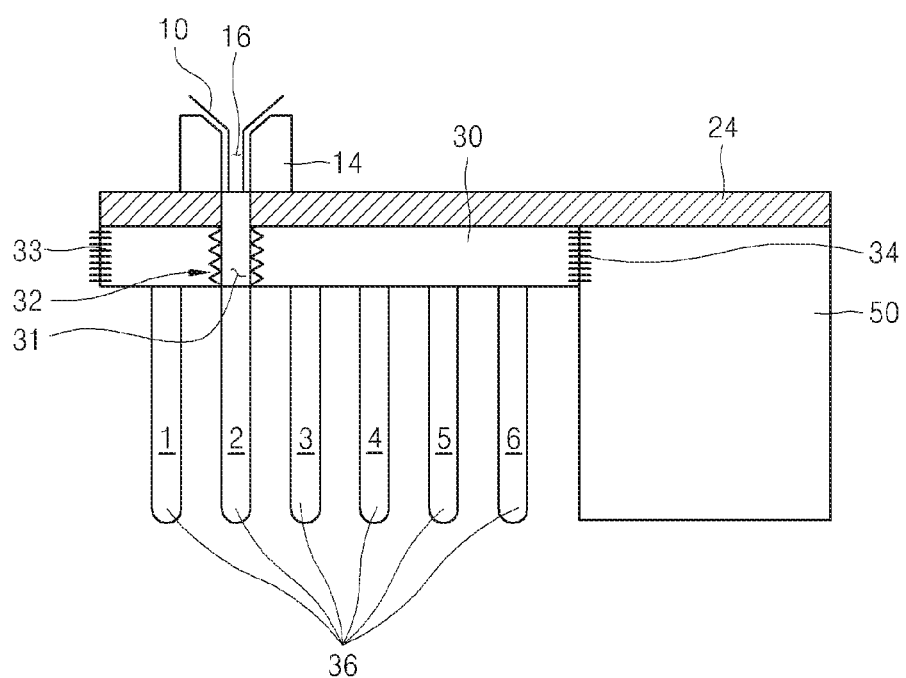
FIG. 2 is a schematic sectional view showing a main part of a time-series sediment trapping device according to the related art.

It should be understood that the details of the same elements as those of FIG. 2 among various elements shown in FIG. 3 will be omitted, and the elements of FIG. 3 are schematically shown differently from those of FIG. 2.

It may be recognized from FIG. 3 that a container fixing older of a time-series sediment trapping device according to an exemplary embodiment of the present invention is provided in the form of a circular holder 38 to fix lower ends of a plurality of time-series sediment trapping containers 36 fixed to a rotation plate 30.

In this case, preferably, the circular polder 38 is fixed by at least one support 37.

The support 37 is fixed to a lower end of the rotation plate 30. In this case, an upper end of the support 37 is screw-coupled to the rotation plate 30 (not shown). In addition, it is more preferred that an upper portion of the support 37 is further fixed to the rotation plate 30 by a nut 37-1 in order to prevent the support 37 from being released from the rotation plate 30.

Preferably, the support 37 is coupled to the circular holder 38 by nuts 37-2 and 37-3. In order to prevent the support 37 from being separated from the circular holder 38, as shown in FIG. 3, the nuts 37-2 and 37-3 are preferably fixed to upper and lower portions of the circular holder 38, respectively, so that locking is doubly performed.

As schematically shown in FIG. 3, the circular holder 38 is preferably formed therein with a plurality of mounting holes 39 to securely mount the time-series sediment trapping containers 36. In addition, preferably, the mounting holes 39 have inner portions enough to smoothly insert outer portions of the time-series sediment trapping containers 36 into the mounting holes 39. Rubber rings (not shown) may be additionally provided in the inner portions of the mounting holes 39 to absorb impact.

In addition, the number of circular holders 38 to be installed may be provided not only to the extent of fixing only lower ends of the time-series sediment trapping containers 36 as shown in drawings, but to the extent of additionally fixing intermediates portions of the time-series sediment trapping containers 36. In this case, a plurality of time-series sediment trapping containers 36 can be actively prevented from being broken or mixed.

In addition, the mounting holes 39 formed in the circular holder 38 are preferably formed corresponding to positions of the time-series sediment trapping containers 36 fixed to the rotation plate 30.

Accordingly, after sediment has been completely trapped into one of the time-series sediment trapping containers 36, the rotation plate 30 is rotated through the rotation of the motor 50 and sediment is trapped into another time-series sediment trapping container 36. In this case, the time-series sediment trapping containers 36 securely mounted in the circular holder 38 may be rotated in the same sequence. In other words, the time-series sediment trapping containers 36 may be prevented by the above rotation.

Hereinafter, the detailed shape of the circular holder 38 will be described with reference to FIG. 4.

Figure 4:
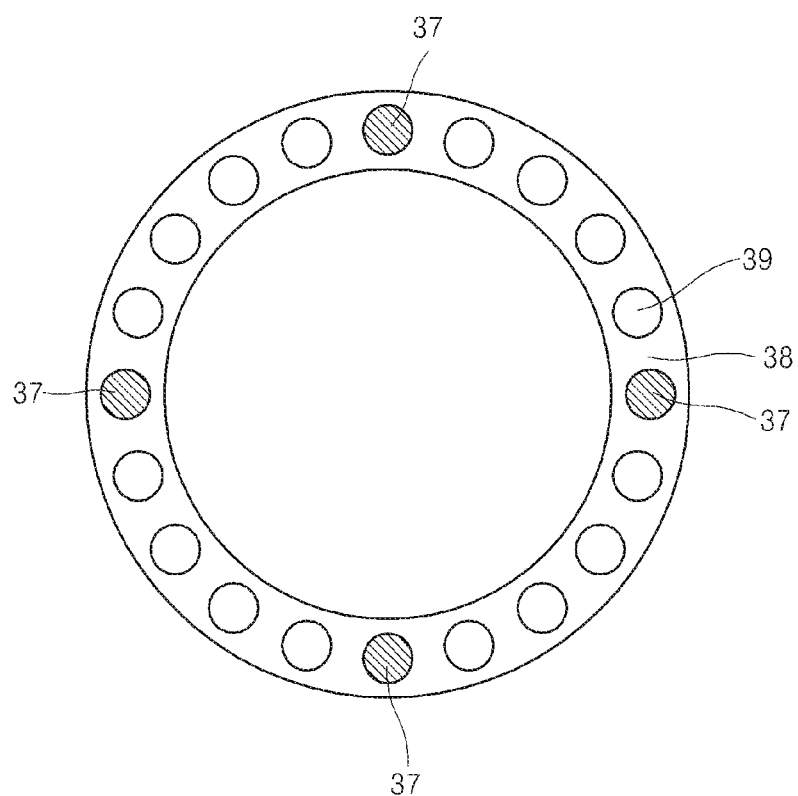
FIG. 4 is a schematic plan view showing a container fixing holder of a time-series sediment trapping device according to an exemplary embodiment of the present invention.

FIG. 4 is a schematic plan view showing a container fixing holder of a time-series sediment trapping device according to an exemplary embodiment of the present invention.

Referring to FIG. 4, the circular holder 38 is formed therein with a support coupling hole to which the support 37 is coupled, and the mounting holes 39. It may be recognized that the circular holder 38 shown in FIG. 4 is substantially matched with the positions of the time-series sediment trapping containers 36 fixed to the rotation plate 30 shown in FIG. 3.

As described above, the mounting holes 39 are preferably formed at positions corresponding to positions to fix the time-series sediment trapping containers 36, and it can be recognized from FIG. 4 that the number of the time-series sediment trapping containers 36 or the mounting holes 39 is 16. Naturally, the number of the time-series sediment trapping containers 36 or the mounting holes 39 is not limited to 16 described above, but may be varied. Accordingly, it should be understood that the number of the time-series sediment trapping containers 36 or the mounting holes 39 is variable.

Although the container fixing holder of the time-series sediment trapping device according to an exemplary embodiment of the present invention has been described for the illustrative purpose, those skilled in the art will appreciate that various modifications, additions and substitutions are possible, without departing from the scope and spirit of the invention as disclosed in the accompanying claims.

INDUSTRIAL APPLICABILITY

According to the present invention, since the time-series sediment trapping container of the time-series sediment trapping device is fixed by the container fixing holder, the time-series sediment trapping container are not broken or missed, so that data can be completely acquired in time series when the time-series sediment is trapped.

The invention claimed is:

1. A container fixing holder of a time-series sediment trapping device including a funnel to collect sediment dropped under water; a frame provided to support and surround the funnel and including at least one rod vertically provided; and a fixing plate coupled to the at least one rod forming the frame on a horizontal plane defined by a lower portion of the funnel, wherein a rotation plate, to which a plurality of time-series sediment trapping containers to trap time-series sediment collected through the funnel are fixedly attached, is formed under the fixing plate, the rotation plate rotates in time series via gear-engagement through rotation of a motor such that the time-series sediment is trapped into the time-series sediment trapping container, and the container fixing holder comprises a circular holder to fix the time-series sediment trapping containers fixedly attached to the rotation plate without shaking.

2. The container fixing holder of claim 1, wherein the time-series sediment trapping containers are fixed to the rotation plate.

3. The container fixing holder of claim 1, wherein at least one support, which extends downward, is fixed to the rotation plate.

4. The container fixing holder of claim 3, wherein the support extending downward from the rotation plate is fixed to the circular holder while extending until the circular holder.

5. The container fixing holder of claim 4, wherein the support is fixed to the rotation plate in screw-type coupling.

6. The container fixing holder of claim 5, wherein the support is further fixed to the rotation plate by a bolt.

7. The container fixing holder of claim 4, wherein the support is fixed to upper and lower portions of the circular holder by a bolt and a nut.

8. The container fixing holder of claim 1, wherein the circular holder is formed therein with a plurality of mounting holes into which the time-series sediment trapping containers are securely mounted.

9. The container fixing holder of claim 8, wherein the mounting holes formed in the circular holder are formed corresponding to positions of the time-series sediment trapping containers.

10. The container fixing holder of claim 1, wherein the fixing plate and the rotation plate include plastic.

11. The container fixing holder of claim 1, wherein the frame is formed in an upper end thereof with a mooring hole to moor the time-series sediment trapping device.

12. The container fixing holder of claim 1, wherein the frame is formed in a lower end thereof with a weight hole to stably drop the time-series sediment trapping device.

* * * * *